United States Patent
Itoh et al.

(10) Patent No.: US 9,947,871 B2
(45) Date of Patent: *Apr. 17, 2018

(54) SURFACE MODIFIER FOR METAL ELECTRODE, SURFACE-MODIFIED METAL ELECTRODE, AND METHOD FOR PRODUCING SURFACE-MODIFIED METAL ELECTRODE

(71) Applicant: SHIN-ETSU CHEMICAL CO., LTD., Tokyo (JP)

(72) Inventors: Yusuke Itoh, Niigata (JP); Ayumu Kiyomori, Niigata (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 194 days.

This patent is subject to a terminal disclaimer.

(21) Appl. No.: 14/647,635

(22) PCT Filed: Nov. 18, 2013

(86) PCT No.: PCT/JP2013/081035
§ 371 (c)(1),
(2) Date: May 27, 2015

(87) PCT Pub. No.: WO2014/084078
PCT Pub. Date: Jun. 5, 2014

(65) Prior Publication Data
US 2015/0295176 A1    Oct. 15, 2015

(30) Foreign Application Priority Data
Nov. 28, 2012 (JP) ................. 2012-259748

(51) Int. Cl.
| | | |
|---|---|---|
| H01L 51/00 | (2006.01) | |
| C07F 7/18 | (2006.01) | |
| H01B 1/08 | (2006.01) | |
| C09D 183/06 | (2006.01) | |
| C09D 183/08 | (2006.01) | |
| H01L 51/44 | (2006.01) | |
| H01L 51/52 | (2006.01) | |
| C08G 77/14 | (2006.01) | |
| C08G 77/26 | (2006.01) | |
| C08G 77/00 | (2006.01) | |
| H01L 51/10 | (2006.01) | |

(52) U.S. Cl.
CPC ........ *H01L 51/0021* (2013.01); *C07F 7/1804* (2013.01); *C07F 7/1836* (2013.01); *C09D 183/06* (2013.01); *C09D 183/08* (2013.01); *H01B 1/08* (2013.01); *C08G 77/14* (2013.01); *C08G 77/26* (2013.01); *C08G 77/80* (2013.01); *H01L 51/102* (2013.01); *H01L 51/442* (2013.01); *H01L 51/5206* (2013.01); *H01L 51/5215* (2013.01); *H01L 51/5221* (2013.01); *Y10T 428/24355* (2015.01); *Y10T 428/265* (2015.01)

(58) Field of Classification Search
None
See application file for complete search history.

(56) References Cited

U.S. PATENT DOCUMENTS

| | | | |
|---|---|---|---|
| 5,951,912 A | 9/1999 | Mercer | |
| 2002/0084553 A1* | 7/2002 | Nun ...................... | C08G 77/24 264/284 |
| 2003/0235933 A1* | 12/2003 | Rantala .................. | G02B 6/132 438/31 |
| 2007/0026580 A1* | 2/2007 | Fujii ................... | H01L 21/0271 438/149 |
| 2008/0042129 A1 | 2/2008 | Nakagawa et al. | |
| 2009/0004772 A1 | 1/2009 | Jinbo et al. | |
| 2010/0230639 A1* | 9/2010 | Yamada ................ | C07C 211/54 252/500 |
| 2011/0248291 A1 | 10/2011 | Jinbo et al. | |
| 2012/0003485 A1 | 1/2012 | Habich et al. | |
| 2014/0147628 A1 | 5/2014 | Kiyomori et al. | |

FOREIGN PATENT DOCUMENTS

| | | |
|---|---|---|
| CN | 1905136 | 1/2007 |
| CN | 101236897 | 8/2008 |

(Continued)

OTHER PUBLICATIONS

CRC Hankbook of Metal Etchants, 1991, Walker et al. p. 321.*

(Continued)

*Primary Examiner* — Peter A Salamon
(74) *Attorney, Agent, or Firm* — Alston & Bird LLP

(57) ABSTRACT

A surface modifier for a metal electrode containing a reactive silyl compound represented by General Formula (1)

$$\text{Rf—X-A-SiR}^1_{3-n}(\text{OR}^2)_n \qquad (1)$$

wherein, Rf is an aryl group having 6 to 10 carbon atoms that may have an alkyl substituent having 1 to 5 carbon atoms or an alkyl group having 1 to 10 carbon atoms, wherein at least one hydrogen atom is replaced with a fluorine atom, X represents a divalent group selected from —O—, —NH—, —C(=O)O—, —C(=O)NH—, —OC(=O)NH—, and —NHC(=O)NH—, or a single bond, A represents a straight chain, branched chain or cyclic aliphatic divalent hydrocarbon group having 1 to 10 carbon atoms, an aromatic divalent hydrocarbon group having 6 to 10 carbon atoms, or a single bond, $R^1$ is a monovalent hydrocarbon group having 1 to 3 carbon atoms, $R^2$ represents a monovalent hydrocarbon group having 1 to 3 carbon atoms, an acetyl group, a propanoyl group, or a hydrogen atom, and n is an integer of 1 to 3, a metal electrode surface-modified with the surface modifier, and a method for producing a surface-modified metal electrode are provided.

10 Claims, No Drawings

(56) References Cited

FOREIGN PATENT DOCUMENTS

| | | | |
|---|---|---|---|
| CN | 102653638 A | 9/2012 | |
| JP | 2001-512779 | 8/2001 | |
| JP | 2005 070369 A | 3/2005 | |
| JP | 2005-158765 A | 6/2005 | |
| JP | 2007-59893 A | 3/2007 | |
| JP | 2007-157752 A | 6/2007 | |
| JP | 2008-130882 A | 6/2008 | |
| JP | 2008-211191 A | 9/2008 | |
| JP | 2012-532813 A | 12/2012 | |
| JP | 2013-153177 | 8/2013 | |
| JP | 2014-507056 A | 3/2014 | |
| KR | 20070014057 | 1/2007 | |
| KR | 20080072571 | 8/2008 | |
| WO | WO 99/07806 | 2/1999 | |
| WO | WO-2006068189 | 6/2006 | |
| WO | WO 2012/117035 A1 | 9/2012 | |
| WO | WO 2012117035 A1 * | 9/2012 | .......... H01M 8/0228 |

OTHER PUBLICATIONS

Extended European Search Report for corresponding European Application No. 13857749.9 dated Oct. 14, 2016.
Office Action for corresponding Japanese Patent Application No. 2013-234929 dated Sep. 16, 2016.
Office Action for Japanese Application No. 2014-550133 dated Jul. 8, 2016.
Office Action for U.S. Appl. No. 14/084,036 dated Jun. 10, 2016.
Office Action for Chinese Application No. 201380061333.9 dated Jun. 2, 2017, 24 pages total.
Office Action from corresponding Chinese Patent Application No. 201310631216.3 dated Sep. 6, 2015.
Yamamoto Takamichi et al.; "*AFM Anodization Lithography on Transparent Conductive Substrates*"; Journal of Nanoscience and Nanotechnology; vol. 8, No. 8; pp. 3833-3842; Dec. 2008.
Chen, H.-Y. et al., *Self-assembled monolayer modification of silver source-drain electrodes for high-performance pentacene organic field-effect transistors*, Organic Electronics, vol. 13 (2012) 593-598.
Extended European Search Report for corresponding European Application No. 13194528.9 dated Feb. 26, 2014, 7 pages.
Gundlach, D. J. et al., *Pentacene TFT With Improved Linear Region Characteristics Using Chemically Modified and Drain Electrodes*, IEEE Electron Device Letters, vol. 22, No. 12 (Dec. 2001) 571-573.
Hatton, R. A. et al., *Organic electroluminescent devices: enhanced carrier injection using an organosilane self assembled monolayer (SAM) derivatized ITO electrode*, Thin Solid Films vol. 394, Elsevier Science B.V., (2001) 292-297.
International Search Report and Written Opinion for corresponding International Application No. PCT/JP2013/081035, dated Feb. 18, 2014.
Lee, J. et al., *Modification of an ITO anode with a hole-transporting SAM for improved OLED device characteristics*, Journal of Materials Chemistry (2002) 3494-3498.
Lee, J. Y., *Relationships between the chemical nature of silanes and device performance of polymer light emitting diodes*, Thin Solid Films, vol. 515, No. 4 Elsevier B. V. (2006) 2705-2708.
Material Matters, Molecular Self-Assembly, Aldrich vol. 1, No. 2 (2006) 1-20.
Mori, T. et al., *Effect of Self-Assembled Monolayer on Electroluminescence Properties of Organic Light-Emitting Diodes*, Japanese Journal of Applied Physics, vol. 47, No. 1 (2008) 455-459.
Office Action for European Application No. EP 13 194 528.9 dated Mar. 1, 2017.

\* cited by examiner

SURFACE MODIFIER FOR METAL ELECTRODE, SURFACE-MODIFIED METAL ELECTRODE, AND METHOD FOR PRODUCING SURFACE-MODIFIED METAL ELECTRODE

FIELD

The present invention relates to a surface modifier for a metal electrode, to a surface-modified metal electrode, and to a method for producing a surface-modified metal electrode.

BACKGROUND

Organic thin film transistors are expected to be utilized in driving circuits for organic light-emitting diodes (OLEDs), radio-frequency ID tags, sensors, and the like, because a low-temperature deposition process is applicable to them and they can be easily deposited on a flexible substrate and the like. Performance of a device depends on the interface between an electrode and an organic semiconductor. That is, it is considered that electrical contact resistance exists between an organic semiconductor layer and an electrode and that the energy difference between the work function of the highest occupied molecular orbital (HOMO) of the organic semiconductor and that of the electrode has a large effect. Gold electrodes, which generally have a work function around 5.1 eV, match well with the HOMO of p-type organic semiconductors and are frequently used. However, research using silver and copper are also underway because of cost issues. Silver electrodes, which have a work function of 4.26 eV and copper electrodes, which have a work function of 4.6 eV, do not match well with organic semiconductors. As a measure to solve this problem, attempts have been made to perform surface treatment on a source-drain electrode to thereby change its work function and to lower the electrical charge injection barrier between the electrode and an organic semiconductor layer.

For example, NPL 1 discloses that an attempt has been made to perform surface treatment of a metal electrode with pentafluorothiophenol to thereby form a self-assembled monolayer (SAM) on the electrode and to change the work function of the electrode surface. Thiols have such features that they form strong bonds on metals and thus have high durability and that a substituent having a high electronegativity such as fluorine increases their work function. Such organic thin film transistors (TFTs) have good characteristics, and solution processes with a high production efficiency can be applicable to the TFTs.

Alternatively, NPL 2 discloses that two-component SAMs of $C_8F_{17}C_2H_4SH$ and $C_{10}H_{21}SH$ are used, and the work function can be desirably regulated by changing the ratio between the two components. Surface modification by use of such two-component SAMs has achieved superior performance to that of organic TFTs including a gold electrode.

NPL 3 discloses that thioacetic acid, which is used for thiol synthesis and tends to be mixed as an impurity, has been intentionally added to thiol to form SAMs, and the influence of the impurity on the SAMs has been investigated. It is indicated that a trace amount of an impurity mixed in thiol causes competitive absorption onto gold and defects are included in the monolayer. In this case, the greater the amount of thioacetic acid, the more defects there are in the monolayer.

Additionally, reactive silanes such as silane coupling agents, as surface treatment agents, can form SAMs on oxide materials such as silicone oxides, titanium oxides, ITOs, aluminum oxides, glass, tin oxides, and germanium oxides, and also on metal materials such as silicon, titanium, and aluminum, via their surface oxide films.

NPL 4 discloses a method for changing the work function by depositing a self-assembled monolayer (F-SAM) of heptadecafluorodecyl triethoxysilane, which is a reactive silane, on an ITO.

CITATION LIST

Non-Patent Literature

NPL 1: IEEE Electron Device Letters 2001, vol. 22, p. 571-573
NPL 2: Organic Electronics, 2012, vol. 13, p. 593-598
NPL 3: Material Matters 2006, vol. 1, No. 2, p. 3-5
NPL 4: Japanese Journal of Applied Physics, 2008, vol. 47, p. 455-459

SUMMARY

However, the thiols disclosed in NPLs 1 and 2, which are useful for changing work functions on a metal surface, are susceptible to impurities as described in NPL 3. In other words, the presence of a trace amount of impurities, mainly precursor compounds, which have not been separated in a thiol purification process, may cause a problem of producing defects in a monolayer, thereby failing to provide constant performance. Purification such as distillation is required to increase the purity, but it is difficult to separate thiol precursors and the like from thiols because of their similar molecular weights. Alternatively, thiols, which are oxidized to be disulfides, have to be stored at a low temperature under an inert atmosphere and have a problem also in storage stability.

In contrast, the reactive silane disclosed in NPL 4 can be bonded with oxide materials having a surface oxide film, but not with metal surfaces having no surface oxide film. No example has been known of forming a silane SAM on a surface of metals having a relatively high work function, in particular, gold, silver, copper, and platinum, to change the work function.

Accordingly, a surface modifier that can appropriately change the work function of an metal electrode and is easily handled and is stable, and a method for surface-modifying a metal electrode using the surface modifier, have been desired.

The present invention has been made in consideration of such circumstances. The present inventors, as a result of intensive research, have found that the problems described above can be solved by modifying a metal surface by a simple treatment to change the work function of the metal surface by using a reactive silane having fluorinated hydrocarbon groups having a specific structure as a surface modifier for a metal electrode, thereby completing the present invention.

That is, the present invention is, according to one embodiment, a surface modifier for a metal electrode including a reactive silyl compound, represented by General Formula (1):

$$Rf\text{—}X\text{-}A\text{-}SiR^1{}_{3-n}(OR^2)_n \qquad (1)$$

wherein,

Rf is an aryl group having 6 to 10 carbon atoms that may have an alkyl substituent having 1 to 5 carbon atoms or an alkyl group having 1 to 10 carbon atoms, wherein at least one hydrogen atom is replaced with a fluorine atom, X represents a divalent group selected from —O—, —NH—, —C(=O)O—, —C(=O)NH—, —OC(=O)NH—, and —NHC(=O)NH—, or a single bond, A represents a straight chain, branched chain or cyclic aliphatic divalent hydrocarbon group having 1 to 10 carbon atoms, an aromatic divalent hydrocarbon group having 6 to 10 carbon atoms, or a single bond, $R^1$ is a monovalent hydrocarbon group having 1 to 3 carbon atoms, $R^2$ represents a monovalent hydrocarbon group having 1 to 3 carbon atoms, an acetyl group, a propanoyl group, or a hydrogen atom, and n is an integer of 1 to 3.

Another aspect according to the present invention is a method for producing a surface-modified metal electrode comprising: a step of bringing a surface modifier for a metal electrode including a reactive silyl compound represented by General Formula (1) into contact with a surface of a metal electrode, and a step of thereby providing a surface-modified metal electrode, wherein the surface work function of the surface-modified metal electrode is greater than the surface work function of the metal electrode before the contact step by 0.20 eV or more.

The surface modifier for a metal electrode according to the present invention is highly effective for increasing the work function of a metal electrode, even though the metal has no sites that can be covalently bonded with reactive silyl groups on its surface. Additionally, the metal electrode surface modified with the surface modifier for a metal electrode does not lose the effect if washed with an organic solvent, and has excellent solvent resistance, heat resistance, and durability. Furthermore, the method for producing a surface-modified metal electrode according to the present invention, which enables production of a surface-modified metal electrode using a easily handled surface modifier for a metal electrode in a simple manner, has a high degree of industrial applicability.

DETAILED DESCRIPTION

The surface modifier for a metal electrode of the present invention is a compound having a reactive silyl group represented by the following General Formula (1):

$$\text{Rf—X-A-SiR}^1{}_{3-n}(\text{OR}^2)_n \quad (1)$$

In General Formula (1), Rf is an aryl group having 6 to 10 carbon atoms that may have an alkyl substituent having 1 to 5 carbon atoms or an alkyl group having 1 to 10 carbon atoms, wherein at least one hydrogen atom is replaced with a fluorine atom.

In the case in which Rf is an aryl group, examples of Rf include substituents in which at least one hydrogen atom in a phenyl or naphthyl group is replaced with a fluorine atom. In particular, from a viewpoint of its tendency to form a dense monolayer, a phenyl group is preferred.

In the case in which Rf is an alkyl group, examples of Rf include substituents in which at least one hydrogen atom in a linear alkyl group such as a methyl group, an ethyl group, an n-propyl group, an n-butyl group, an n-pentyl group, an n-hexyl group, an n-heptyl group, an n-nonyl group, an n-octyl group, and an n-decyl group, or a branched alkyl group such as an isopropyl group, an isobutyl group, a sec-butyl group, a tert-butyl group, an isopentyl group, a 2-pentyl group, a 3-pentyl group, and a tert-pentyl group is replaced with a fluorine atom. In particular, from a viewpoint of achieving a sufficient effect of increasing the work function, linear alkyl groups having 4 to 8 carbon atoms such as an n-butyl group, an n-hexyl group, and an n-octyl group are preferred.

In the case in which Rf is an aryl group having alkyl substituents, the number of the alkyl substituents are preferably 1 to 5, more preferably 1 to 3. Examples of the alkyl substituents include a methyl group, an ethyl group, an n-propyl group, and an isopropyl group. In particular, from a viewpoint of increasing the density of the modifier on the metal electrode surface, a methyl group is preferred. In the case in which Rf is an aryl group having alkyl substituents, fluorine atoms may be directly bonded to the aromatic ring constituting Rf, or may be bonded to the alkyl substituents.

Both in the cases in which Rf is an aryl group and in which Rf is an alkyl group, the number of fluorine atoms contained in Rf is preferably 1 to 20, more preferably 1 to 15.

Specific examples of Rf include linear fluoroalkyl groups such as a trifluoromethyl group, a pentafluoroethyl group, a heptafluoropropyl group, a nonafluorobutyl group, a tridecafluorohexyl group, a nonadecafluorooctyl group, a 2,2,2-trifluoroethyl group, a 2,2,3,3,3-pentafluoropropyl group, a 2,2,3,3,4,4,5,5,5-nonafluoropentyl group, and a 2,2,3,3,4,4,5,5,6,6,7,7-tridecafluoroheptyl group. 2,2,3,3,4,4,5,5,6,6,7,7,8,8,9,9,9-hexadecafluorononyl group, a 3,3,3-trifluoropropyl group, a 3,3,4,4,4-pentafluorobutyl group, a 3,3,4,4,5,5,6,6,6-nonafluorohexyl group, a 3,3,4,4,5,5,6,6,7,7,8,8,8-tridecafluorooctyl group, a 3,3,4,4,5,5,6,6,7,7,8,8,9,9,10,10,10-heptadecafluorodecyl group, a 4,4,4-trifluorobutyl group, a 4,4,5,5,5-pentafluoropentyl group, a 4,4,5,5,6,6,7,7,7-nonafluoroheptyl group, a 4,4,5,5,6,6,7,7,8,8,9,9,9-tridecafluorononyl group, a 5,5,5-trifluoropentyl group, a 5,5,6,6,6-pentafluorohexyl group, a 5,5,6,6,7,7,8,8,8-nonafluorooctyl group, a 5,5,6,6,7,7,8,8,9,9,10,10,10-tridecafluorodecyl group, a 6,6,6-trifluorohexyl group, a 6,6,7,7,7-pentafluoroheptyl group, a 6,6,7,7,8,8,9,9,9-nonafluorononyl group, a 7,7,7-trifluoroheptyl group, a 7,7,8,8,8-pentafluorooctyl group, a 7,7,8,8,9,9,10,10,10-nonafluorodecyl group, a 9,9,9-trifluorononyl group, and a 9,9,10,10,10-pentafluorodecyl; and fluoroaryl groups such as a pentafluorophenyl group, a 2,3,4,5-tetrafluorophenyl group, a 2,3,5,6-tetrafluorophenyl group, a 2,3,5-trifluorophenyl group, a 2,4,5-trifluorophenyl group, a 3,4,5-trifluorophenyl group, a 2,4,6-trifluorophenyl group, a 2,4-difluorophenyl group, a 3,4-difluorophenyl group, a 3,5-difluorophenyl group, a 2-fluorophenyl group, a 3-fluorophenyl group, a 4-fluorophenyl group, a 3-trifluoromethylphenyl group, a 4-trifluoromethylphenyl group, a 3,5-bis(trifluoromethyl)phenyl group, a 3-trifluoromethylnaphthyl group, a 4-trifluoromethylnaphthyl group, and a 3,5-bis(trifluoromethyl)naphthyl group.

In General Formula (1), X represents a divalent group selected from —O—, —NH—, —C(=O)O—, —C(=O)NH—, —OC(=O)NH—, and —NHC(=O)NH— or a single bond. In particular, a case in which X is a single bond is preferred in respect of heat resistance and durability of the surface modified layer.

In General Formula (1), A represents a straight chain, branched chain or cyclic aliphatic divalent hydrocarbon group having 1 to 10 carbon atoms, an aromatic divalent hydrocarbon group such as benzene or substituted benzene and naphthalene having 6 to 10 carbon atoms, or a single bond. Specific examples of A include a single bond; a straight chain, branched chain or cyclic aliphatic divalent hydrocarbon group, such as a methylene group, a 1,2-ethanediyl group, a 1,1-ethanediyl group, a 1,2-ethenediyl group, a 1,1-ethenediyl group, a 1,3-propanediyl group, a 1,2-propanediyl group, a 2-methyl-1,3-propanediyl group, a 1,3-butanediyl group, a 1,4-butanediyl group, a 1,5-pentanediyl group, a 1,6-hexanediyl group, a 1,4-cyclohexanediyl group, a 1,7-heptanediyl group, a 1,8-octanediyl group, a 1,9-nonanediyl group, and a 1,10-decanediyl group; an aromatic divalent hydrocarbon group, such as a 1,3-benzenediyl group, a 1,4-benzenediyl group, a 2-methyl-1,4-benzenediyl group, a 3-methyl-1,4-benzenediyl group, a 2,5-dimethyl-1,4-benzenediyl group, a 1,4-naphthalenediyl group, a 2,6-naphthalenediyl group, a 2,7-naphthalenediyl group, a 4-ethylbenzene-1,2-diyl group, and a 4-propylbenzene-1,3-diyl group.

From a viewpoint of regulating the coverage of a surface modifier, it can be said that the more bulky the substituent A, the lower the coverage can be, and the less bulky the substituent A, the higher the coverage can be. Thus, from a viewpoint of increasing the coverage, as for aliphatic divalent hydrocarbon groups with the same carbon number, straight chain divalent hydrocarbon groups are more preferred over branched chain or cyclic divalent hydrocarbon groups. Additionally, as for aromatic divalent hydrocarbon groups, from a viewpoint of increasing the coverage, over bulky groups with a substituent in the ortho position to the silicon atom, less bulky groups with no substituents are preferred.

In General Formula (1), $R^1$ is a monovalent hydrocarbon group having 1 to 3 carbon atoms. Specific examples of $R^1$ include a methyl group, an ethyl group, a propyl group, and an isopropyl group. Considering the balance between the reactivity and the stability of the compound of Formula (1), and from a viewpoint of increasing the coverage, a methyl group is most preferred.

$R^2$ represents a monovalent hydrocarbon group having 1 to 3 carbon atoms, an acetyl group, a propanoyl group, or a hydrogen atom. Examples of the monovalent hydrocarbon group of $R^2$ include, for example, a methyl group, an ethyl group, a propyl group, and an isopropyl group. Considering the balance between the reactivity and the stability of compounds of Formula (1), a methyl group and an ethyl group are preferred.

In General Formula (1), n is an integer of 1 to 3. A compound represented by General Formula (1) has at least one reactive silyl group. It is thus presumed that the compounds represented by General Formula (1) are each other hydrolyzed between their molecules to form thin films. It is believed that these films coat the metal surface to increase the work function.

Specific examples of the compounds represented by General Formula (1) include, but not limited to, the following: 3,3,3-trifluoropropyltrimethoxysilane, 3,3,4,4,4-pentafluorobutyltrimethoxysilane, 3,3,4,4,5,5,5-heptafluoropentyltrimethoxysilane, 3,3,4,4,5,5,6,6,6-nonafluorohexyltrimethoxysilane, 3,3,4,4,5,5,6,6,7,7,7-undecafluoroheptyltrimethoxysilane, 3,3,4,4,5,5,6,6,7,7,8,8,8-tridecafluorooctyltrimethoxysilane, 3,3,4,4,5,5,6,6,7,7,8,8,9,9,9-pentadecafluorononyltrimethoxysilane, 3,3,4,4,5,5,6,6,7,7,8,8,9,9,10,10,10-heptadecafluorodecyltrimethoxysilane, 3,3,3-trifluoropropyltriethoxysilane, 3,3,4,4,4-pentafluorobutyltriethoxysilane, 3,3,4,4,5,5,5-heptafluoropentyltriethoxysilane, 3,3,4,4,5,5,6,6,6-nonafluorohexyltriethoxysilane, 3,3,4,4,5,5,6,6,7,7,7-undecafluoroheptyltriethoxysilane, 3,3,4,4,5,5,6,6,7,7,8,8,8-tridecafluorooctyltriethoxysilane, 3,3,4,4,5,5,6,6,7,7,8,8,9,9,9-pentadecafluorononyltriethoxysilane, 3,3,4,4,5,5,6,6,7,7,8,8,9,9,10,10,10-heptadecafluorodecyltriethoxysilane, pentafluorophenyltrimethoxysilane, pentafluorobenzyltrimethoxysilane, 2-(pentafluorophenyl)ethyltrimethoxysilane, 3-(pentafluorophenyl)propyltrimethoxysilane, 4-(pentafluorophenyl)butyltrimethoxysilane, 5-(pentafluorophenyl)pentyltrimethoxysilane, 3,4,5-trifluorophenyltrimethoxysilane, 3,4,5-trifluorobenzyltrimethoxysilane, 2-(3,4,5-trifluorophenyl)ethyltrimethoxysilane, 3-(3,4,5-trifluorophenyl)propyltrimethoxysilane, 4-(3,4,5-trifluorophenyl)butyltrimethoxysilane, 5-(3,4,5-trifluorophenyl)pentyltrimethoxysilane, 4-fluorophenyltrimethoxysilane, 4-fluorobenzyltrimethoxysilane, 2-(4-fluorophenyl)ethyltrimethoxysilane, 3-(4-fluorophenyl)propyltrimethoxysilane, 4-(4-fluorophenyObutyltrimethoxysilane, 5-(4-fluorophenyl)pentyltrimethoxysilane, pentafluorophenyltriethoxysilane, pentafluorobenzy)triethoxysilane, 2-(pentafluorophenyl)ethyltrimethoxysilane, 3-(pentafluorophenyl)propyltriethoxysilane, 4-(pentafluorophenyl)butyltriethoxysilane, 5-(pentafluorophenyl)pentyltriethoxysilane, 3,4,5-trifluorophenyltriethoxysilane, 3,4,5-trifluorobenzyltriethoxysilane, 2-(3,4,5-trifluorophenyl)ethyltriethoxysilane, 3-(3,4,5-trifluorophenyl)propyltriethoxysilane, 4-(3,4,5-trifluorophenyObutyltriethoxysilane, 5-(3,4,5-trifluorophenyl)pentyltriethoxysilane, 4-fluorophenyltriethoxysilane, 4-fluorobenzyltriethoxysilane, 2-(4-fluorophenyl)ethyltriethoxysilane, 3-(4-fluorophenyl)propyltriethoxysilane, 4-(4-fluorophenyl)butyltriethoxysilane, 5-(4-fluorophenyl)pentyltriethoxysilane, pentafluorophenyltripropoxysilane, pentafluorophenyltriisopropoxysilane, pentafluorophenylethoxydimethoxysilane, pentafluorophenyldiethoxymethoxysilane, pentafluorophenylisopropoxydimethoxysilane, pentafluorophenyldiisopropoxymethoxysilane, pentafluorophenyltriacetoxysilane, pentafluorophenyltri(propanoyloxy)silane, pentafluorophenylhydroxydimethoxysilane, pentafluorophenylhydroxydiethoxysilane, pentafluorophenylhydroxydiisopropoxysilane, pentafluorophenyldihydroxymethoxysilane, pentafluorophenyltrihydroxysilane, pentafluorophenyl(methyl)dimethoxysilane, pentafluorophenyl(methyl)diethoxysilane, pentafluorophenyl(ethyl)dimethoxysilane, pentafluorophenyldimethylmethoxysilane, pentafluorophenyldimethylethoxysilane, pentafluorophenyldiethylmethoxysilane, and pentafluorophenyldiisopropylhydroxysilane.

As a compound represented by General Formula (1), from a viewpoint of the heat resistance and the durability of the surface modified layer, a compound wherein X in General Formula (1) is a single bond and A is a straight chain divalent hydrocarbon group, or a compound wherein X is a single bond and A is an aromatic divalent hydrocarbon group is preferred. Additionally, a compound wherein n is 3, and $R^2$ is a monovalent hydrocarbon group, in particular, $R^2$ is a methyl group or an ethyl group, and particularly, a compound wherein n is 2, $R^1$ is a methyl group, and $R^2$ is a monovalent hydrocarbon group, in particular, $R^2$ is a methyl group or an ethyl group are preferably used. This is from a viewpoint that the balance between the stability and the reactivity between molecules of the compound of General Formula (1) is good. Additionally, from a viewpoint of regulating coverages of surface modifiers detailed below, it can be said that generally, the more bulky the substituent A and/or $R^1$, the lower the coverage can be, and the less bulky the substituent A and/or $R^1$, the higher the coverage can be. Thus, from a viewpoint of increasing the coverage, a non-bulky substituent can be selected as A and/or $R^1$.

A surface modifier according to this embodiment includes the above described compound having a reactive silyl group represented by General Formula (1) as a main ingredient. The main ingredient may be composed of only one among the above described compounds having a reactive silyl group represented by General Formula (1), or two or more compounds may be mixed in combination to form the main ingredient. In the case in which two or more compounds are combined, the combination is optional. For example, compounds can be combined, from a viewpoint of achieving desired physical properties of the electrode surface by combining several modifiers differing in characteristics, such as compounds with different values of work function, compounds with modifying densities to the electrode surface different from that of the surface modifier, compounds having a reaction rate with the electrode surface different from that of the modifier, and compounds having modifier molecules different in size and length in the case in which the surface has been modified with one compound alone. The combinations include, for example, but are not limited to, 3-(pentafluorophenyl)propyltrimethoxysilane and 3-(4-fluorophenyl)propyltrimethoxysilane, 2-(pentafluorophenyl)ethyltrimethoxysilane and 3-(4-fluorophenyl)propyltrimethoxysilane, 3-(pentafluorophenyl)propyltriethoxysilane and 3-(2,4-difluorophenyl)propyltrimethoxysilane, 3-(pentafluorophenyppropyltrimethoxysilane and 3-(4-fluorophenyl)propyldimethylmethoxysilane, 3-(4-fluorophenyl)propyltrimethoxysilane and 3-(pentafluorophenyl)propyl(methyl)dimethoxysilane, 3-(4-trifluoromethylphenyl)propyltrimethoxysilane and 3-(4-fluorophenylpropyl)trimethoxysilane, 6-(pentafluorophenyl)hexyltrimethoxysilane and 3-(3,4,5-trifluorophenyl)propyltrimethoxysilane, and 3-(pentafluorophenyl)propyltrimethoxysilane and 3-(pentafluorophenyl)propyldimethoxydihydroxysilane and 3-(pentafluorophenyl)propylmethoxydihydroxysilane.

A surface modifier according to this embodiment may be composed of a main ingredient only, not including other ingredients. In this case, the possibility in which the compounds containing a reactive silyl group represented by General Formula (1), which are the main ingredient, are mutually hydrolyzed between their molecules to form a uniform thin film to thereby come in contact with the electrode surface becomes maximized. In particular, it is preferable that the surface modifier not include water or low-volatile ionic compounds, which may cause self-polycondensation of the surface modifier before use. However, as long as the work function can be maintained at an appropriate value without inhibiting formation of self-assembled monolayers, the surface modifier is not prevented from containing other ingredients.

In addition, as additives to enhance the reactivity of the surface modifier in intermolecular hydrolysis reaction, acids such as acetic acid and nitric acid and bases such as triethylamine, which are used for preparing solutions of silane coupling agents in the known art, can be added as catalysts in a proportion of, preferably 5% by mass or less, more preferably 0.1 to 1% by mass. In the case in which catalysts are added, it is preferable to use catalysts composed of volatile substances that can be easily removed from the electrode surface after modification.

Now, a method for producing a surface modifier according to this embodiment is described. The method for producing a surface modifier according to this embodiment includes steps of: providing a compound containing a reactive silyl group represented by General Formula (1), which is a main ingredient, and optionally mixing a plurality of compounds constituting the main ingredient and additives.

Some of the compounds containing a reactive silyl group represented by General Formula (1), which are the main ingredient, are commercially available. Thus, such commercially available compounds can be the main ingredient as is or after purification, as appropriate. Alternatively, in accordance with the prior art references, those skilled in the art can synthesize these compounds, which can be purified to the extent required for surface modifiers, for example, 99% or more, to provide the main ingredient.

The surface modifier according to the present invention can be used in a method for surface modifying a metal electrode. In this context, the method for surface-modifying a metal electrode can also be referred to as a method for producing a surface-modified metal electrode. The method for producing a surface-modified metal electrode will be described below.

That is, the present invention, according to yet another embodiment, includes a method for producing a surface-modified metal electrode using the above-described surface modifier including the steps of: bringing a surface modifier into contact with a surface of a metal electrode, and thereby obtaining a surface-modified metal electrode. There may be optionally provided a step of removing extra surface modifier and removing moisture on the surface-modified metal electrode surface after the contact step.

In the method for producing a surface-modified metal electrode according to this embodiment, the production method is performed by surface modification of the surface of the metal electrode. The metal electrode may be made of a single metal or of an alloy. The work function of the metal constituting the metal electrode before surface modification is preferably 4.0 eV or more. This is because, if the work function is less than 4.0 eV, the work function after modification may not reach a sufficiently high value. Specific examples of the metal include, but are not limited to, gold, silver, copper, iron, lead, zinc, nickel, platinum, aluminum, silver-indium alloys, and aluminum-zinc alloys. From a viewpoint of electrical conductivity, a particularly preferred metal electrode is gold, silver, or copper.

The method for producing a surface-modified metal electrode according to the present invention is performed by a step of bringing at least one surface modifiers containing a reactive silyl compound represented by General Formula (1) into contact with the surface of the above-described metal electrode. This step is hereinafter referred to as "the contact step". Since the above-described surface modifier that can be used in this embodiment is highly stable in air, the contact step can be performed in air to enable deposition. Contact methods are optional, and examples include a method for bringing a liquid surface modifier into contact with a metal electrode in a liquid phase and a method for bringing vapor of a surface modifier into contact with a metal electrode in a gas phase. The liquid surface modifier in the contact method in a liquid phase may be a surface modifier of which temperature is increased to a desired temperature at which the surface modifier turns into liquid, or optionally, may be a solution formed by appropriately diluting the surface modifier with a solvent.

The temperature of the surface modifier in performing the contact step in a liquid phase can be set in a range of about 0 to 250° C., but the temperature is preferably about 15 to 80° C., and more preferably about 20 to 60° C. In the case in which the contact step is performed in a gas phase, the temperature and the pressure are set such that the vapor pressure of the surface modifier is preferably 0.01 Pa or higher, more preferably 0.1 Pa or higher.

The treatment period of the contact step, in the case in which the step is performed in a liquid phase, is one hour to three weeks, preferably two hours to two weeks, more preferably four hours to one week. In the case in which the step is performed in a gas phase, it may be 20 hours to three weeks, preferably 10 hours to two weeks, more preferably five hours to one week.

The amount of a surface modifier used in the contact step is preferably $1\times10^{-6}$ to 10 mol, more preferably $1\times10^{-5}$ to 5 mol, and further preferably $1\times10^{-4}$ to 3 mol per 1 $m^2$ of the surface area of an electrode to be modified. Use of a large excess of a surface modifier is preferred from a viewpoint of increasing the surface modification rate. The surface modifier not used for modifying the electrode can be collected to be reused. In this context, the surface area of the electrode herein refers to the effective surface area of the electrode. The effective surface area means a surface area with the roughness, the texture and the fine configuration of the electrode surface considered. Taking into account of the molecular size of the surface modifier according to the present invention, the effective surface area can be calculated in consideration of the surface roughness of about 1 nm and the fine shape to determine the amount of the surface modifier to be used.

The average thickness of the surface modified layers of the surface-modified electrode of the present invention is preferably 3 nm or less, more preferably 0.5 to 3 nm, and further preferably 1 to 2.5 nm. In the case in which the surface-modified layer has a thickness less than 0.5 nm, a sufficient modification effect may not be achieved due to a small amount of change in the work function, whereas, in the case of a thickness more than 3 nm thick, transfer of electric charges by the electrode may be inhibited. Such a thickness can be determined depending on the size of the compound represented by General Formula (1) constituting the surface modifier according to the present invention and the arrangement and the orientation state on the electrode surface. An example of the method for measuring the average thickness of surface-modified layers includes a polarization analysis method (ellipsometry).

The surface modifier used in the contact step is preferably not diluted with a solvent such as organic solvents. In the case in which a solution diluted with a solvent is used, the metal surface may be insufficiently modified, and an appropriate effect may not be achieved.

In performing the contact step, water may coexist. In the case in which reactive groups bonded to silicon atoms of a compound containing a reactive silyl group represented by General Formula (1), which is the main ingredient, are alkoxy groups or acyloxy groups, silanol is formed in hydrolysis reaction to facilitate reaction between the molecules of compounds containing a reactive silyl group represented by General Formula (1). In the case in which a compound containing a reactive silyl group represented by General Formula (1) is silanol, addition of water is not necessarily needed. In performing the contact step in a liquid phase, water can be added to a liquid surface modifier. In performing the contact step in a liquid phase, water can be added to a surface modifier or its solution. In performing the contact step in a gas phase, water can be added as water vapor. Alternatively, water absorbed on the electrode surface before the contact step is performed can be employed. In this case, contact operation can be performed without adding water. For example, in a case in which the contact angle of water on the electrode surface is determined to be 30° or less, which corresponds to a hydrophilic state, it is believed that water vapor in the atmosphere, if any, is supplied to the electrode surface and a sufficient amount of water is adsorbed on the electrode surface.

In the contact step, it is preferred that the amount of water to be added in the case in which water is added to the surface modifier is normally 0.01 to 1 mol per 1 mol of the surface modifier used in the contact step to minimize self-polycondensation of the surface modifier.

In the above described contact step, at least one surface modifier represented by General Formula (1) is used. Thus, for example, a plurality of surface modifiers can be mixed to perform the contact step. A mode of the contact step in which a plurality of surface modifiers are mixed can be performed similarly both in a liquid phase and in a gas phase. Alternatively, the contact step can also be performed using simultaneously a plurality of surface modifiers without mixing. The mode of the contact step performed using simultaneously a plurality of surface modifiers without mixing is applied to, in particular, a case of gas phase contact. Furthermore, sequential contact steps can be performed using a plurality of surface modifiers. Also in the case in which the sequential contact steps can be performed similarly both in a liquid phase and in a gas phase. These modes have an advantage that the work function of the electrode surface can be finely adjusted because a plurality of surface modifiers can be used for modifying the surface of the metal electrode.

Post-treatment steps such as heating, washing, and drying may be optionally performed on the surface-modified metal electrode after the contact step. In particular, in the case in which the contact step is performed in a liquid phase, it is preferable that an excess surface modifier be removed from the electrode by washing with solvent. In this case, washing efficiency is increased by simultaneous ultrasonic irradiation. Specifically, the step can be performed by immersing the metal electrode after completion of the contact step in washing solvent contained in ultrasonic cleaner. Alternatively, a step of removing moisture adsorbed on the surface may be performed as a post-treatment step. Specifically, the step can be performed by heating the surface-modified metal electrode on a hot plate or in an oven. The heating temperature and time in this case can be freely determined by one skilled in the art. The heating temperature and time are preferably 40 to 300° C., more preferably 60 to 250° C. for preferably 1 to 120 minutes, more preferably 5 to 60 minutes. The heating may be performed in the atmosphere, or in inert gases such as nitrogen and argon.

It should be noted that, in the method for producing a surface-modified metal electrode of the present invention, it is preferable not to perform a step of activating the electrode surface before performing the contact step. For example, in the case in which UV ozone treatment, oxygen plasma treatment, or the like is performed, an oxide film is formed on the metal electrode surface, and the desired effect may not be achieved.

The method for producing a surface-modified metal electrode or the method for surface-modifying a metal electrode using the above-described surface modifier can provide a surface-modified metal electrode by bringing the above-described surface modifier into contact with at least one surface of the metal electrode for coating. On the surface of the surface-modified metal electrode, a self-assembled monolayer has been theoretically formed. According to another aspect, the present invention relates to a surface-modified metal electrode. The surface-modified metal electrode according to the present invention may have very useful physical properties as, for example, organic thin film transistors by including a surface-modified layer formed with a surface modifier.

Specifically, the surface work function of the surface-modified metal electrode of the present invention significantly increases compared to the surface work function of an untreated metal electrode. The amount of change in the surface work function, that is, the difference between the surface work function of a surface-modified metal electrode after modification and the surface work function of an untreated metal electrode before modification, if measured in the atmosphere, is preferably +0.20 eV to +2.0 eV, further preferably +0.30 eV to +1.8 eV. The surface work function of metal electrodes can be measured with, for example, a Kelvin probe (KP), vacuum ultraviolet photoelectron spectroscopy (UPS), and photoelectron yield spectroscopy (PYS). Substantially similar values can be obtained if the values are obtained with any measurement method. It is preferable to have an amount of change in the surface work function within the above described numerical range, if any measurement method is used.

Note that the preferable properties of surface-modified metal electrodes according to the present invention have been described in the above. However, a surface-modified metal electrode according to the present invention may be an electrode including a surface-modified layer formed by being coated the above-described surface modifier. It is not necessary for the electrode to have all the numerical properties.

EXAMPLES

The surface modifier and the method for producing a surface-modified metal electrode of the present invention will be more specifically described below, referring to Examples and Comparative Examples.

Examples 1 to 3 (Surface Modification Treatment by a Gas Phase Method)

Silver electrode and copper electrode surfaces were modified by a gas phase method using a surface modifier composed solely of each compound shown in Table 1 and its legend. 300 mg (0.9 to 1 mmol (depending on the compound used in each Example)) of each surface modifier was placed in a resin cup, which was placed in the center of the bottom of a glass container with a lid having an internal volume of 350 mL. As an electrode sample, silver foil or copper foil (manufactured by Alfa Aesar, thickness: 0.25 mm) cut into a size of 15 mm×15 mm was used, and the silver foil or copper foil was disposed around the resin cup. After the lid of the glass container was closed, the gas phase contact step was performed at room temperature. When the gas phase contact step was performed, the vapor pressures of all the surface modifiers were about 1 Pa or more. After each treatment period, the metal substrate was removed from the container. The surface-modified metal substrates were subjected to surface work function measurement. The results are shown in Table 1.

Examples 4 to 6 (Surface Modification Treatment By a Liquid Phase Method)

Silver electrode and copper electrode surfaces were modified by a liquid phase method using a surface modifier composed solely of each compound shown in Table 1 and its legend. 3 ml of each surface modifier was placed in a 20 ml vial bottle, into which silver foil or copper foil cut into a size of 15 mm×15 mm as an electrode sample was placed such that the whole surface was immersed in the liquid surface. The sample was drawn after being immersed in this solution for a predetermined period, ultrasonically washed with an acetone solution, and dried at room temperature by blowing nitrogen.

Comparative Examples 1 to 3

Metal electrodes were modified by a gas phase method and a liquid phase method in the same manner as in Examples, using 2-phenylethyltrimethoxysilane (B-1) that is not substituted with fluorine as the surface modifier.

<Changes in the Surface Work Function>

Changes in the surface work function were measured in the atmosphere using an Atmospheric Humidity Kelvin Probe (manufactured by KP Technology, Ltd., KP020). Amounts of change before and after surface modification were determined on the basis of the value of the surface work function measured on an untreated metal substrate.

TABLE 1

|  | Surface modifier | Treatment period | Treatment method | Type of substrate | Amount of change in surface work function (eV) |
|---|---|---|---|---|---|
| Example 1 | A-1 | One week | Gas phase method | Silver foil | +0.43 |
| Example 2 | A-2 | One week | Gas phase method | Silver foil | +0.78 |
| Example 3 | A-2 | One week | Gas phase method | Copper foil | +0.61 |
| Example 4 | A-1 | One week | Liquid phase method | Silver foil | +0.81 |
| Example 5 | A-1 | Five hours | Liquid phase method | Silver foil | +0.49 |
| Example 6 | A-1 | One week | Liquid phase method | Copper foil | +0.28 |
| Comparative Example 1 | B-1 | One week | Gas phase method | Silver foil | No change |
| Comparative Example 2 | B-1 | One week | Gas phase method | Copper foil | No change |
| Comparative Example 3 | B-1 | One week | Liquid phase method | Copper foil | No change |

A-1: 3-(pentafluorophenyl)propyltrimethoxysilane
A-2: 3,3,4,4,5,5,6,6,7,7,8,8,8-tridecafluorooctyltrimethoxysilane
B-1: 2-phenylethyltrimethoxysilane In Examples 1 to 6 in which the surface modifiers of the present invention were used, all the surface work functions of the metal electrodes increased compared to Comparative Examples 1 to 3 in which treatment was performed with the compound that is not substituted with fluorine.

INDUSTRIAL APPLICABILITY

The surface modifier for a metal electrode of the present invention, which allows the surface work function of metal electrodes to be adjusted, can be employed for manufacturing organic electronic devices such as organic thin film transistors, organic electroluminescent elements, and organic solar cells.

The invention claimed is:

1. A surface modifier for a metal electrode comprising a reactive silyl compound represented by General Formula (1)

$$Rf\text{—}X\text{-}A\text{-}SiR^1{}_{3-n}(OR^2)_n \quad (1)$$

wherein,
Rf is an aryl group having 6 to 10 carbon atoms that may have an alkyl substituent having 1 to 5 carbon atoms, wherein at least one hydrogen atom is replaced with a fluorine atom,
X represents a divalent group selected from —O—, —NH—, —C(=O)O—, —C(=O)NH—, —OC(=O)NH—, and —NHC(=O)NH—, or a single bond,
A represents a straight chain, branched chain or cyclic aliphatic divalent hydrocarbon group having 1 to 10 carbon atoms, an aromatic divalent hydrocarbon group having 6 to 10 carbon atoms,
$R^1$ is a monovalent hydrocarbon group having 1 to 3 carbon atoms,
$R^2$ represents a monovalent hydrocarbon group having 1 to 3 carbon atoms, an acetyl group, a propanoyl group, or a hydrogen atom, and
n is an integer of 1 to 3.

2. The surface modifier for a metal electrode according to claim 1, wherein X is a single bond in General Formula (1).

3. The surface modifier for a metal electrode according to claim 1, wherein the metal electrode is a metal having a work function before surface modification of 4.0 eV or more.

4. The surface modifier for a metal electrode according to claim 1, wherein the metal electrode is selected from the group consisting of gold, silver, copper, iron, lead, zinc, nickel, platinum, aluminum, silver-indium alloys, and aluminum-zinc alloys.

5. A surface-modified metal electrode formed by coating a metal electrode with a surface modifier for a metal electrode comprising a reactive silyl compound represented by General Formula (1) according to claim 1.

6. The surface-modified metal electrode according to claim 5, wherein the metal electrode is a metal having a work function before surface modification of 4.0 eV or more.

7. The surface-modified metal electrode according to claim 6, wherein the metal electrode is selected from the group consisting of gold, silver, copper, iron, lead, zinc, nickel, platinum, aluminum, silver-indium alloys, and aluminum-zinc alloys.

8. A method for producing a surface-modified metal electrode, comprising the steps of:
bringing a surface modifier for a metal electrode comprising a reactive silyl compound represented by General Formula (1) according to claim 1 into contact with a surface of the metal electrode, and
thereby obtaining a surface-modified metal electrode,
wherein the surface work function of the surface-modified metal electrode is greater by 0.20 eV or more than the surface work function of the metal electrode before the contact step.

9. The method for producing a surface-modified metal electrode according to claim 8, wherein the contact step is performed by a gas phase contact method in which the surface of the metal electrode is exposed to an atmosphere in which the surface modifier is vaporized.

10. The method for producing a surface-modified metal electrode according to claim 8, wherein the contact step is performed by a liquid phase method in which the metal electrode is immersed in the liquid surface modifier.

* * * * *